United States Patent [19]
Rink et al.

[11] Patent Number: 5,154,707
[45] Date of Patent: * Oct. 13, 1992

[54] METHOD AND APPARATUS FOR EXTERNAL CONTROL OF SURGICAL LASERS

[76] Inventors: Dan L. Rink, 6008 Auburn St., Oakland, Calif. 94618; John L. Rink, 1741-C Mason St., San Francisco, Calif. 94133; Howard S. Cohen, 2001 Lincoln St., Berkeley, Calif. 94709

[ * ] Notice: The portion of the term of this patent subsequent to Aug. 21, 2007 has been disclaimed.

[21] Appl. No.: 557,096

[22] Filed: Jul. 26, 1990

Related U.S. Application Data

[63] Continuation-in-part of Ser. No. 523,473, May 14, 1990, Pat. No. 5,057,099, which is a continuation-in-part of Ser. No. 265,565, Nov. 1, 1988, Pat. No. 4,950,268, which is a continuation-in-part of Ser. No. 19,755, Feb. 27, 1987.

[51] Int. Cl.$^5$ ............................................. A61N 5/06
[52] U.S. Cl. ........................................ 606/12; 606/11; 606/15; 606/16; 128/398; 128/898
[58] Field of Search ................................ 606/10–19, 606/27–31; 128/395, 397, 398, 898

[56] References Cited

U.S. PATENT DOCUMENTS

| | | | |
|---|---|---|---|
| 4,209,017 | 6/1980 | Shaw | 606/28 |
| 4,454,882 | 6/1984 | Takano | 606/11 |
| 4,543,477 | 9/1985 | Doi et al. | 606/12 |
| 4,564,012 | 11/1986 | Shimada et al. | 606/12 |
| 4,646,737 | 3/1987 | Hussein et al. | 606/7 |
| 4,950,268 | 8/1990 | Rink | 606/12 |

FOREIGN PATENT DOCUMENTS

8501869  5/1985  World Int. Prop. O. ............ 606/11

Primary Examiner—David M. Shay

[57] ABSTRACT

A method and apparatus used in combination with an existing laser for controlling the temperature of a laser powered tool includes a temperature control device coupled between the output of the laser and the optical fiber delivery system to monitor the temperature of the optical fiber delivery system and attenuate the laser output power to achieve a desired temperature level. The device establishes a beam path and provides a beam deflector that is variably positioned in the beam path to deflect a variable portion of the laser beam toward a laser wavelength-absorbing heat sink. An infrared detector is directed to receive emissions from the laser tool, and electronic circuitry processes the signal from the infrared detector to determine the temperature in the delivery system and generate an actuator signal to position the beam deflector so that beam deflection is increased or decreased to achieve a predetermined, desirable temperature level in the delivery system. A photodetector is disposed to receive ambient light from the area near the laser operation, and a time discrimination circuit receives the photodetector signal to determine if laser radiation is escaping into the area. The system causes laser shutdown if laser light is present in the area, so that operating personnel may eliminate the use of laser safety eyewear.

17 Claims, 7 Drawing Sheets

Figure_1

Figure_2

Figure_3

Figure_4

Figure_5

Figure_6

Figure_7

METHOD AND APPARATUS FOR EXTERNAL CONTROL OF SURGICAL LASERS

REFERENCE TO RELATED APPLICATION

This application is a continuation-in-part of application Ser. No. 07/523,473, filed May 14, 1990, now U.S. Pat. No. 5,057,099 which is a continuation-in-part of application Ser. No. 07/265,565, filed Nov. 1, 1988, now U.S. Pat. No. 4,950,268, issued Aug. 21, 1990 to John Rink, which is a continuation-in-part of application Ser. No. 07/019,755, filed Feb. 27, 1987, for which priority is claimed.

BACKGROUND OF THE INVENTION

In recent years the field of medicine has witnessed the application of lasers for therapeutic treatment of a variety of diseases and conditions. Laser energy conducted through a flexible waveguide such as an optical fiber has been used successfully for hemostasis, photodynamic destruction of some forms of tumors, removal of epidermal growths and abnormalities, and the like.

Lasers have also been adapted for use in surgical procedures, and surgical devices have been built, tested, and sold commercially. However, some drawbacks in laser devices for surgical use have been noted in the prior art. Surgical lasers are generally controlled grossly by presetting an output power level which is deemed appropriate for a particular surgical procedure and laser surgical tool, based on empirical knowledge. This preset power approach achieves results that are far less than optimal for many types of laser tools and procedures. For example, U.S. Pat. Nos. 4,693,244 and 4,736,743 discuss the use of a bare optical fiber connected to a laser and used to cut tissue. It is noted that if the bare fiber end contacts the tissue being cut, the fiber becomes fouled, the transmission efficiency decreases, more heat is generated in the fiber, thermal runaway ensues, and the fiber quickly heats to the point of material failure. One attempted solution to this problem in the prior art is to use the fiber end in a non-contact mode, thereby avoiding contamination of the fiber output end. However, contamination is difficult to avoid in practice, due to the fact that the fiber must be held very close to the tissue target, and tissue contact is unavoidable. A single contact with tissue will often result in fiber failure. Also, the smoke and vapor arising from the laser beam impact site can contaminate the fiber end without any contact with the tissue itself.

Another attempt to solve this problem has been the provision of a transparent tip secured to the output end of the optical fiber, the tip being formed of a material such as sapphire that is tolerant of extremely high temperatures. If the tip becomes fouled or coated with carbonized material, it will not be heated to the point of material failure. Several manufacturers make available surgical optical tips having differing cutting configurations. However, even sapphire can be fractured by the high temperatures and temperature transitions experienced at the optical fiber output end. Moreover, sapphire or any similar material is expensive and difficult to manufacture, and the surgical tips can be reused only a few times.

A surgical tip, as well as a bare optical fiber end, may be provided with a constant flow of gas or liquid to prevent overheating and to remove some of the inevitable contamination. However, in some procedures gas cooling can create the risk of embolism in the patient; liquid cooling can cause such problems as fluid distension, fluid absorption through the surgical wound, and the like.

The simplest practical solution available in state of the art surgical lasers is to limit the laser power to a level that cannot damage the optical fiber. Ironically, this approach requires that a laser capable of delivering high power; e.g., 120 watts of beam energy, must often be limited to 30 or 40 watts output or less to preserve the optical fiber integrity. Alternatively, the optical fiber output end must be constantly immersed in a laser-transparent liquid, such as water, during operation, or the tip must remain in contact with the tissue during operation so that the tissue cools the fiber tip. These conditions are difficult to achieve in practice.

It should be noted that there are thousands of surgical lasers installed in hospitals and medical institutions, and that many of them are unable to control the temperature of the delivery system which utilizes the laser output. Furthermore, there are no devices available in the prior art that could be easily retrofitted to existing surgical lasers to enhance their effectiveness by adding a temperature control function to the lasers to protect the delivery systems.

Another drawback to the use of lasers in general is that laser safety eyewear (filter goggles and shielded filter spectacles) is required to protect the eyes of all personnel in the operating area. Failure to use such protection can result in permanent eye damage. However, goggles and shielded spectacles often interfere with ophthalmic spectacles worn by personnel, and severely narrow the field of vision. Moreover, in surgical procedures, where sterile conditions must be maintained, the surgeon and assistant cannot touch the unsterile laser safety eyewear to remove or put them on, nor to adjust them when necessary. Because of this annoyance, some surgeons abrogate the safety rules and refuse to wear the safety eyewear. There is no laser safety feature available in the prior art to alleviate the need for laser safety eyewear.

SUMMARY OF THE PRESENT INVENTION

The present invention generally comprises a method and apparatus for adding a temperature control function to existing surgical lasers. A salient feature of the invention is the provision of an external temperature control device coupled between the output of the laser and the optical fiber delivery system to monitor the temperature of the optical fiber delivery system and attenuate the laser output power to achieve a desired temperature level. The temperature control device may be used to prevent heating of the optical fiber beyond its structural tolerance or a preset limit. Thus the problems known in the prior art associated with contamination of the optical fiber output end, and the resulting thermal runaway, are obviated, and the use of expensive laser surgical cutting tips is eliminated. The optical fiber output end may also be maintained at a predetermined temperature level which is optimized for a particular surgical or medical procedure. Moreover, most existing surgical lasers can be retrofitted with the invention to realize the enhanced surgical cutting effects that are provided by a temperature control system.

The temperature control device may comprise housing having an input connector to receive the laser beam output, and an output connector to secure an optical fiber delivery system. A beam path is established between the input and output connectors, whereby substantially all of the incident laser beam may be coupled into the output connector. The beam path includes a selectively reflective element that reflects the laser wavelength from the input connector toward the output connector, but transmits infrared radiation from the delivery system and output connector to an infrared sensing device, such as a photodiode or phototransistor. Also placed in the beam path is an interrupter device that periodically interrupts the laser beam transmission to the output connector. During the interruption interval, the photodetector signal is monitored and processed to detect the infrared radiation conducted retrograde from the delivery system, from which the temperature of the delivery system is inferred.

It should be noted that the temperature level detected by the invention represents the hottest portion of the optical fiber delivery system. Generally speaking, the hottest portion usually comprises the distal output end of the delivery system, whether a free beam or closed end device. This is due to the fact that at the output end the light energy is usually converted to heat, either by interaction with tissue or absorption by the distal end. For free beam devices, the distal end usually becomes contaminated during use, transmission efficiency decreases, and the contaminants heat very quickly in the presence of the laser beam.

Also placed in the beam path is a beam deflector which is variably positioned in the beam path to deflect a variable portion of the laser beam toward a laser wavelength-absorbing heat sink. The beam deflector may be driven by a piezoelectric actuator, stepper motor, voice coil actuator, or the like. The invention includes electronic circuitry that processes the photodetector signal to determine the temperature in the delivery system, and which generates an actuator signal to position the beam deflector so that beam deflection is increased or decreased to achieve a predetermined, desirable temperature level in the delivery system.

For example, when the infrared radiation exceeds a predetermined threshold indicative of an unacceptably high temperature within the beam delivery path, the detector signal exceeds a threshold and causes the invention to move the beam deflector partially into the beam path. The threshold temperature may be set below the temperature at which the optical fiber material is damaged. Thus, for example, if the optical fiber output end is used to cut, ablate, or coagulate, and becomes coated with debris or carbonized material, the contaminating material will cause absorption of laser radiation at the fiber end and create a localized hot spot. When the hot spot temperature approaches the threshold of thermal damage to the optical fiber, the laser energy conducted to the delivery system is reduced by the beam deflector before the fiber can be damaged. The effective laser power is cut back to a level which continues operation but does not damage the fiber. After a short time, the continued operation usually causes the contaminants to burn away, the infrared signal diminishes, the beam deflector is withdrawn from the beam path, and operating power increases.

Alternatively, in a laser surgical apparatus having an optical fiber delivery system with an output end that is heated by the laser beam passing therethrough, the detector signal may be used to control the beam deflector so that the output end is maintained at a preset temperature that is optimum for the procedure being undertaken. In either case, the laser is set to run at a fixed power level that is greater than the power requirements anticipated for any procedure to be undertaken, and the beam deflector selectively diverts excess laser energy from the beam path. The excess energy is absorbed in the heat sink and transferred to the surroundings by convection and radiation.

In another aspect of the invention, there is provided a laser safety system than detects the presence of laser radiation in the area of the laser operation, so that operating personnel may work without laser safety eyewear. The system includes a photosensor tuned to the wavelength of the laser and directed to receive ambient light in the area surrounding the laser operation. The photosensor is connected to a time discrimination circuit to detect a decreasing amplitude in the laser wavelength, corresponding to the cessation of a laser pulse or initial blockage of the laser beam by the beam interrupter described previously. The photosensor signal is processed electronically so that only an abrupt negative change in the amplitude of the narrow band of the laser output, occurring coincidentally with the beam interrupter sensor signal, will cause an output pulse. The output pulse is fed to the solid state switch connected in series with the remote interlock system of the laser, so that the pulse opens the remote interlock circuit and causes immediate shutoff of the laser. Thus any laser light escaping into the area near the laser operation will cause laser shutoff.

DESCRIPTION OF THE PREFERRED EMBODIMENT

The present invention generally comprises an external laser controller adapted to be retrofit to existing lasers, including surgical lasers. The controller is designed to measure the temperature of the laser surgical delivery system in real time, and to attenuate the laser energy transmitted to the laser surgical delivery system in response to the measured temperature and in accordance with the desired temperature. The controller is designed to enhance the effectiveness of laser surgical delivery systems by permitting the use of higher laser power levels while alleviating the risk of damage to the delivery system due to the increased power.

Figure 1:
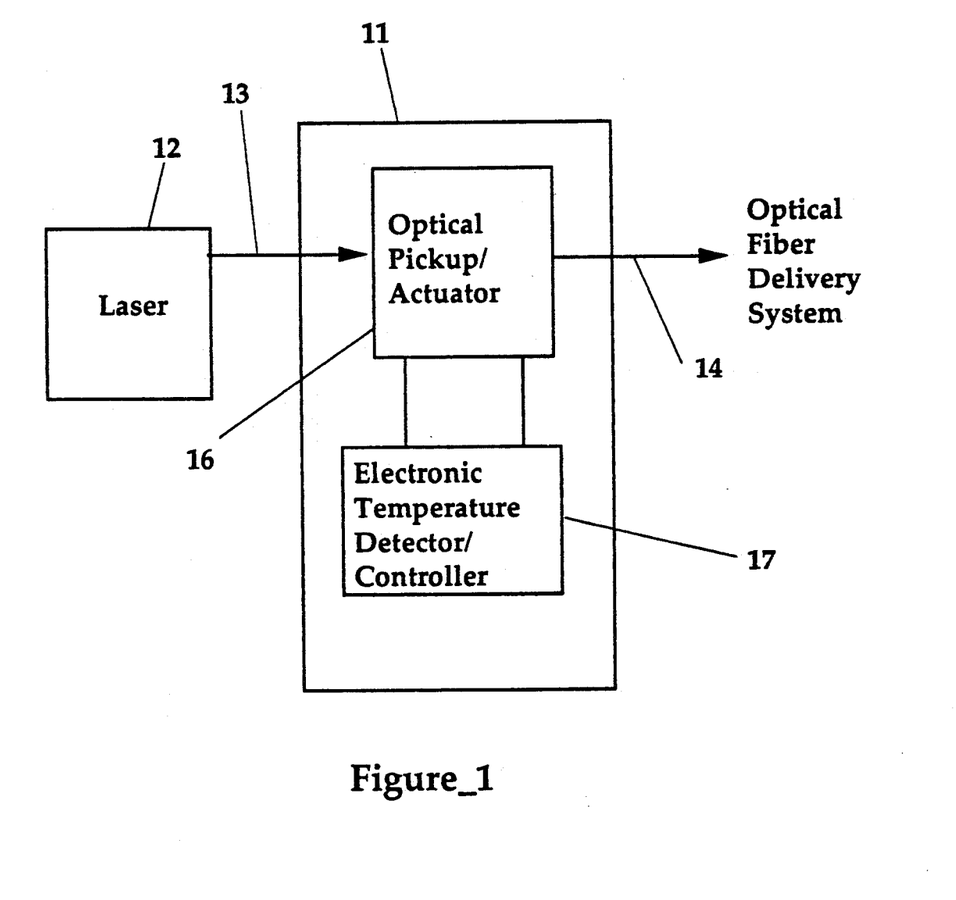
FIG. 1 is a functional block diagram of the external laser controller of the present invention.

With regard to FIG. 1, the invention includes an external laser control apparatus 11 adapted to be used with an existing laser 12. The laser 12 may generally comprise any laser having any known form of lasing medium, such as gas, dye, optically pumped solid state, and the like. Generally speaking, in the surgical field many prior art lasers provide controls that permit the selection of output energy, pulse duration, continuous mode, and the like. However, many lasers have no provision for modulating the output energy level or power in accordance with the temperature of the delivery system receiving the laser energy, either to achieve operation within a desired temperature range, or to set a maximum temperature to prevent thermal damage to the delivery system.

The laser output 13 is received by the apparatus 11 at an input port, and an optical fiber delivery system is coupled to an output port 14 on the apparatus. The laser output 13 passed through an optical pickup/actuator 16 within the apparatus, the device 16 including at least a photo sensitive detector directed to receive optical radiation from the delivery system. The detector may be selected to have increased sensitivity in the infrared band, although this characteristic is not necessary. Currently available commercial optical fibers attenuate infrared radiation from materials heated to less than approximately 200° C., so that measurement of temperatures below that level is not available. However, the future development of optical fibers having broader transmission characteristics will alleviate this limitation. The device 16 is also designed to selectively attenuate the transmission of laser energy to the output port 14, so that the proportion of laser power conducted to the delivery system may be decreased or increased as required.

The apparatus 11 further includes an electronic temperature detector/controller circuit 17 coupled to the device 16. The circuit 17 includes the infrared detector and other detectors within the apparatus, as well as signal processing circuitry and logic circuitry to operate the actuator in the device 16 that selectively attenuates the laser energy transmission through the apparatus.

It should be noted that the apparatus 11 is a stand-alone assembly designed to be retrofitted to existing lasers, and may be designed to be easily removable from operative association with a laser. The apparatus 11 comprises merely a small assembly that is connected optically only to the laser output port and the delivery system input connector, and electrically only to utility power and to the remote interlock system of the existing laser.

Figure 2:
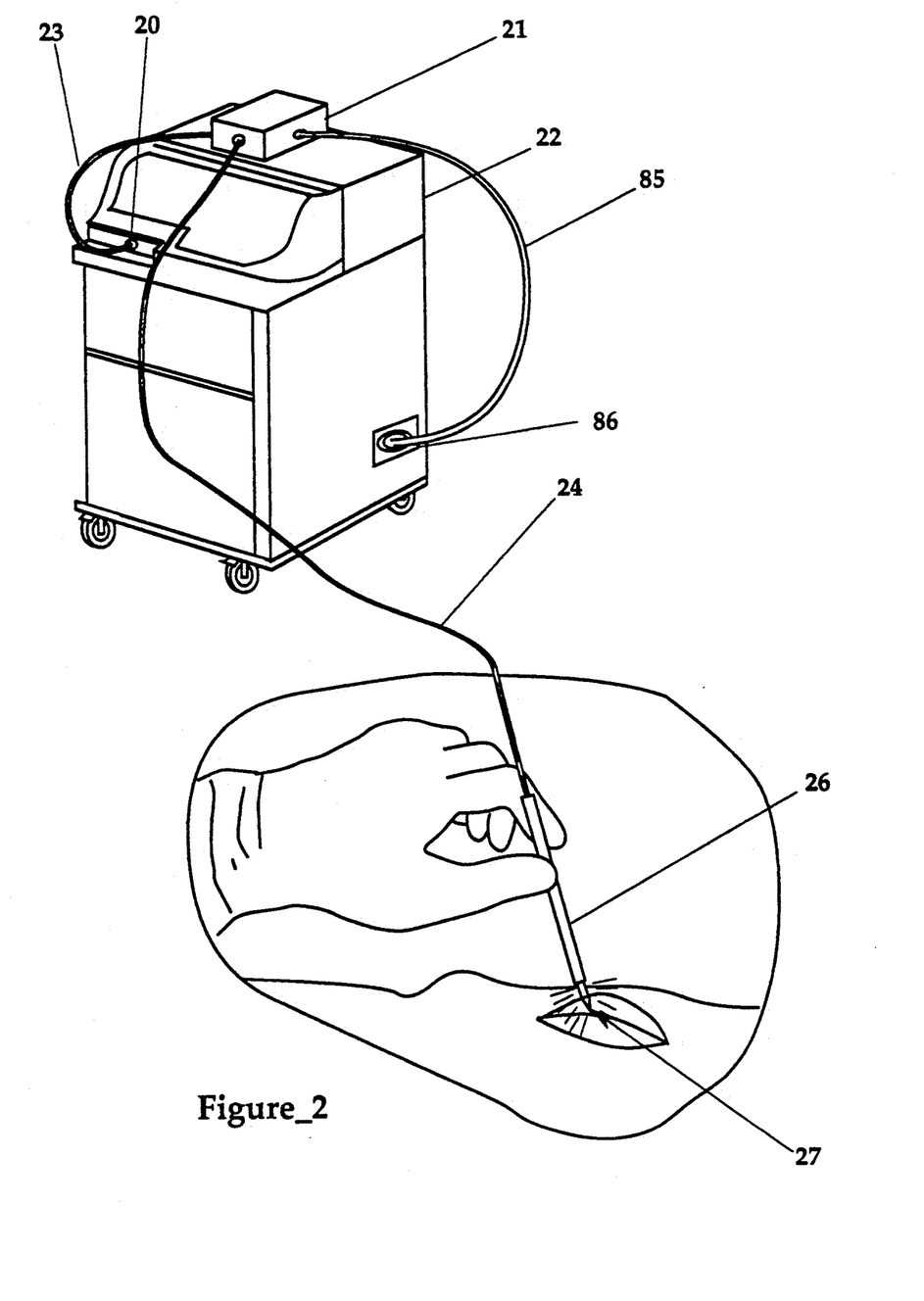
FIG. 2 is a perspective view of the external laser controller of the present invention, shown in use with a surgical laser and a laser surgical tool.

With regard to FIG. 2, one embodiment of the present invention includes a small enclosure 21 disposed to be supported on (or adjacent to) an existing, prior art laser 22. The laser 22 may comprise a medical laser used for surgical and other therapeutic purposes, with a typical output power of 10-150 watts. The laser includes an output connector 20, such as the industry standard SM or ST type connectors, which is provided by the manufacturer to connect the laser output to an optical fiber delivery system. An optically conductive guide 23 is connected from the output connector 20 to an input port on the enclosure 21. An optical fiber delivery system 24 is connected to the output port of the device of the invention to conduct the laser energy to a surgical tool 26. The tool 26 generally includes a distal tip 27 that is shaped or otherwise adapted to perform a therapeutic function on a patient, such as surgical cutting, tissue ablation, coagulation, hemostatis, or the like. The apparatus within the enclosure 21 is adapted selectively and variably to attenuate the laser power conducted therethrough in order to protect the delivery system 24-27 from thermal damage while permitting the delivery system to operate at optimal power levels. The apparatus also permits operation of the delivery system within a predetermined temperature range, according to the requirements of the procedure and limitations of the delivery system. These added control features enhance the effectiveness of most laser surgical optical fiber delivery systems known in the prior art, by increasing cutting rate while decreasing cutting force, permitting the use of higher laser power for coagulation and ablation, and reducing fouling of the distal tip portion of the surgical instrument.

Figure 3:
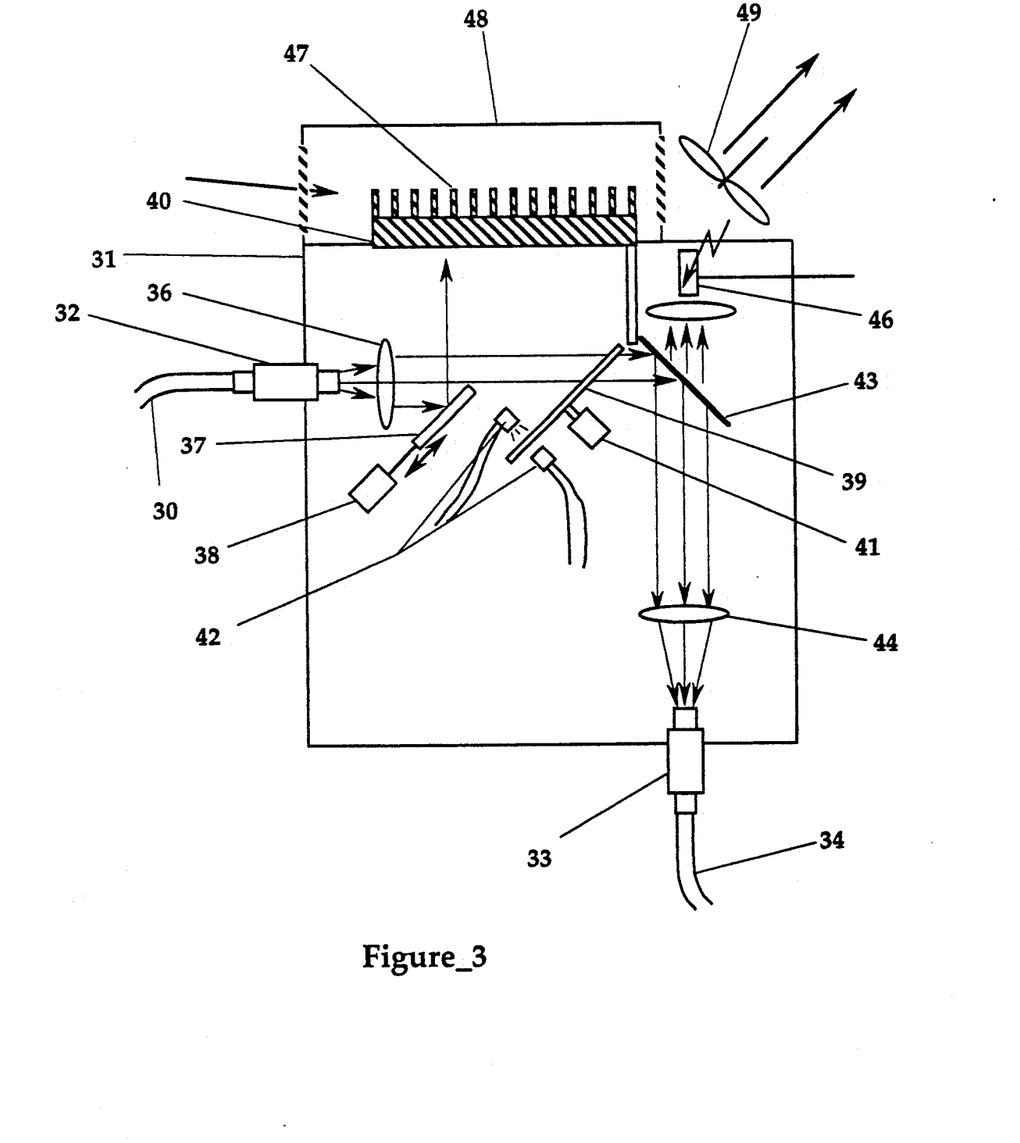
FIG. 3 is a schematic diagram of the external laser controller of the present invention.

With regard to FIG. 3, one embodiment of the optical pickup/actuator 16 shown in FIG. 1 includes an enclosure 31 similar to the enclosure 21 described with reference to FIG. 2. The apparatus includes an input connector 32, such as a standard SMA or ST type connector common the prior art, to which an optical fiber light guide 30 is secured. The light guide 30 is connected at its other end to the output port of an existing laser light source. The apparatus further includes an output connector 33, also a standardized optical connector, to which an optical fiber delivery system 34 is connected. Alternatively, the connectors 32 and/or 33 may comprise a unique bayonet connector, as described in co-pending U.S. patent application Ser. No. 07/532,884, filed Jun. 4, 1990 by Dan Rink and commonly assigned.

Within the enclosure 31, an optical path is defined between the connectors 32 and 33 for the purpose of transmitting the laser energy to the optical fiber delivery system. The laser energy entering the enclosure 31 at the connector 32 diverges according to the numerical aperture of the light guide 30. The light energy impinges on collimating lens 36, which is configured to form a collimated beam of laser light. The beam then passes a beam attenuator 37. In the preferred embodiment the attenuator 37 comprises a reflective panel secured to an extendable actuator 38 and oriented at a substantial angle with respect to the collimated beam. The extendable actuator 38 may comprise any quick response mechanism that can drive the reflective panel reciprocally in the panel plane to extend to a variable amount into the collimated beam path. As the reflective panel extends further into the beam path and eclipses an increasing portion of the laser beam, more of the beam is reflected by the panel towards an absorptive heat sink 40. Thus the portion of the beam that is transmitted beyond the attenuator is decreased. Conversely, the attenuator 37 may be withdrawn completely from the beam path to allow virtually uninterrupted transmission of the laser energy.

Also interposed in the beam path is a beam interrupter device 39. In the preferred embodiment the device 39 may comprise a mechanical shutter that is closed briefly and periodically to block the laser beam. The shutter may comprise a rotating arm or rotating transparent disk having a narrow opaque portion disposed to block the entire beam path completely and briefly. The mechanical shutter may be rotated through the beam path by a motor 41, so that the beam is interrupted periodically for a short interval, on the order of 5% of the time or less and at least once per second. An optical transducer 42 or similar position sensor detects the passing of the opaque portion of the shutter 39, and the signal from the transducer is connected to the electronic circuit of the invention, as will be described in the following description. The opaque portion of the shutter 39 is preferably highly reflective, so that the laser beam blocked by the shutter is also reflected toward the absorptive heat sink 40.

The mechanical shutter 39 may be rotated by a motor 41 at a generally constant rate, and an optical position sensor 42 is disposed to detect the passage of the opaque portion of the shutter through a predetermined position with respect to the laser beam path. The signal from the sensor 42 is conducted to the electronic circuit of the invention, as described below.

Another element interposed in the laser beam path is a selectively reflecting mirror 43 which is disposed at 45° to the beam path and directs the laser beam toward the output connector 33. The mirror 43 is constructed to reflect optical energy at the laser wavelength with an efficiency greater than 99.9%, but to be far more transparent to infrared wavelengths in the operating temperature range of the surgical tool. The laser beam is reflected by mirror 43 toward condensing lens 44, which focuses the laser beam into the output optical connector 33.

The apparatus includes a photodetector 46 disposed on the opposite side of the mirror 43 with respect to the incident laser beam. It is significant to note that the photodetector is directed through the mirror toward the output connector 33, so that it may receive optical energy from the delivery system 34 if the optical energy is not within the reflective bandwidth of the mirror. Specifically, the photodetector is tuned to receive infrared radiation from the delivery system in a portion of the spectrum corresponding to the expected temperature range of the delivery system; i.e. 200° C. to greater than 1000° C. The output signal of the photodetector 46 is conducted to the electronic circuit of the invention, as described below.

It may be appreciated that the selectively reflective mirror 43 may be replaced by other optical devices for selecting the infrared emissions of the delivery system. A filtering system combined with a beam splitter, as is known in the prior art, could be used with equal effect.

Figure 4:
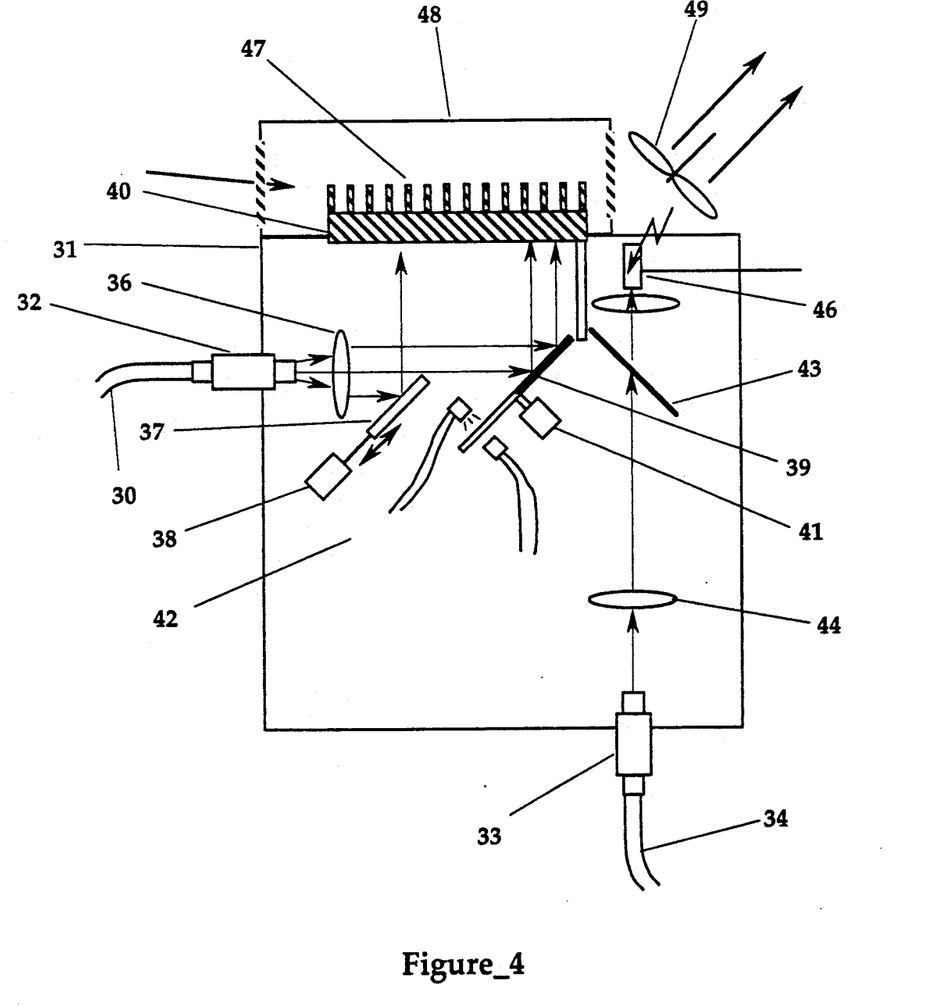
FIG. 4 is a schematic view of the external laser controller, as in FIG. 3, showing the device disposed to receive a temperature reading of the surgical laser tool delivery system.

With reference to FIG. 4, it may be appreciated that the shutter 39 periodically moves into the laser beam path and deflects the entire beam toward the absorptive heat sink 40. In the brief interval in which the laser beam is completely eclipsed, the photodetector receives an infrared signal from the heated portions of the optical fiber delivery system and does not receive any laser radiation either directly or indirectly. The signal generated by the photodetector 46 is proportional to the received infrared signal, and the photodetector signal is processed by the electronic circuit of the invention. The circuit ascertains the temperature of the optical fiber delivery system, and determines if the temperature is within a preset range or within a preset maximum. Based on these determinations, the circuit drives the actuator 38 to deflect more or less of the laser beam. The laser beam is thus attenuated to achieve a desired temperature condition in the optical fiber delivery system.

It may be appreciated that the laser light source must be required to generate more power that would be required if the optical fiber delivery system were connected directly to the laser. However, it is noted that most laser systems known in the prior art are capable of generating far more power than can be utilized safely by prior art optical fiber delivery systems, and the amount of laser power purposely wasted by the present invention is far less than the unused capacity of a typical prior art laser light source.

The laser power deflected from the laser beam path by the attenuator 37 and the interrupter 39 is converted to heat by the heat sink 40. The heat sink may be provided with cooling fins 47 extending into a shroud 48, with a fan system arranged to move air through the shroud 48. The heat from the attenuated laser beam is thus thrown off to the ambient air; it may be appreciated that the amount of heat generated is generally less than a typical table lamp, and is easily dispersed to the environment.

Figure 5:
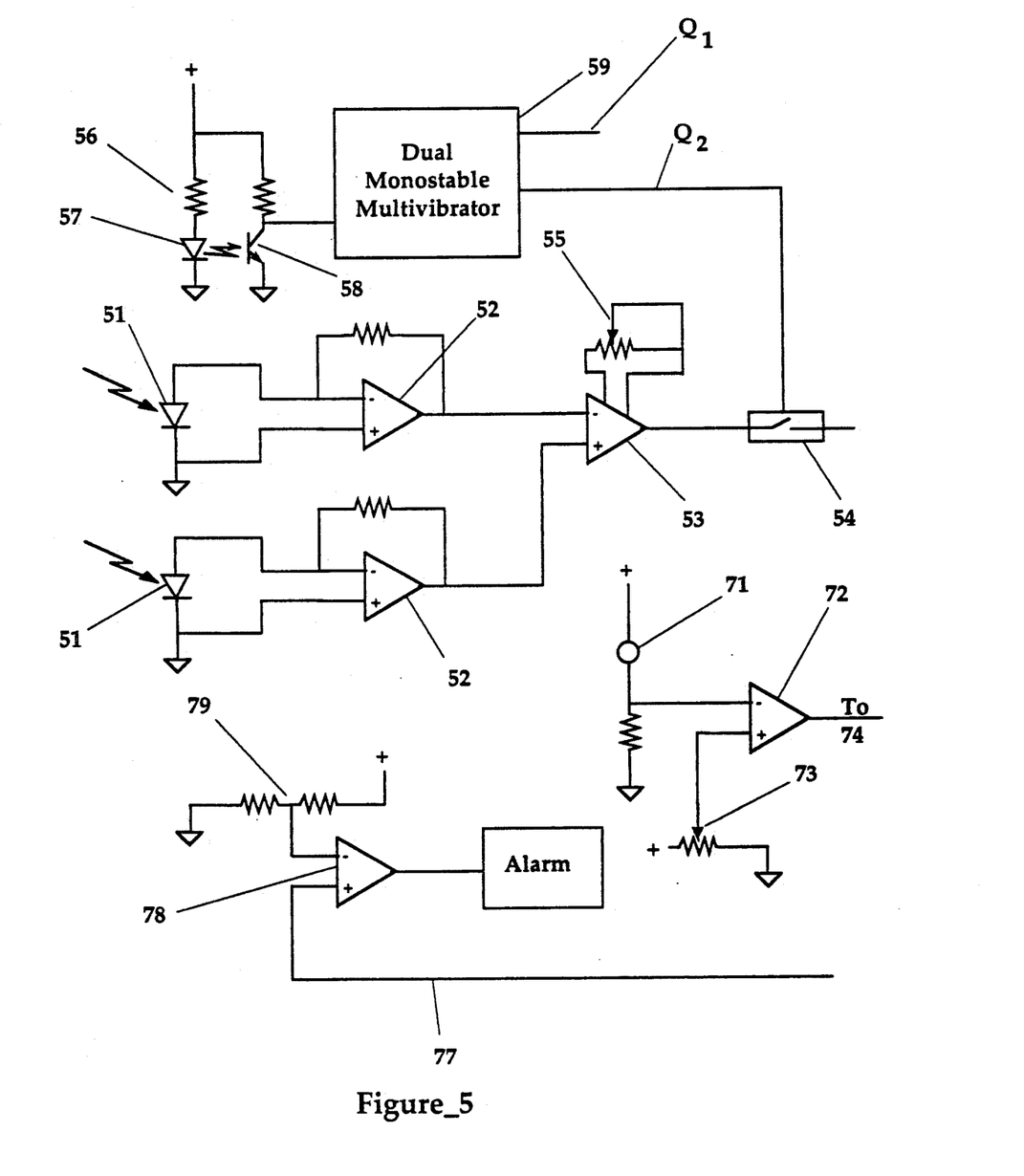
FIGS. 5 and 6 are adjacent segments of a schematic diagram of an electronic circuit used in the external laser controller of the present invention.
Figure 6:
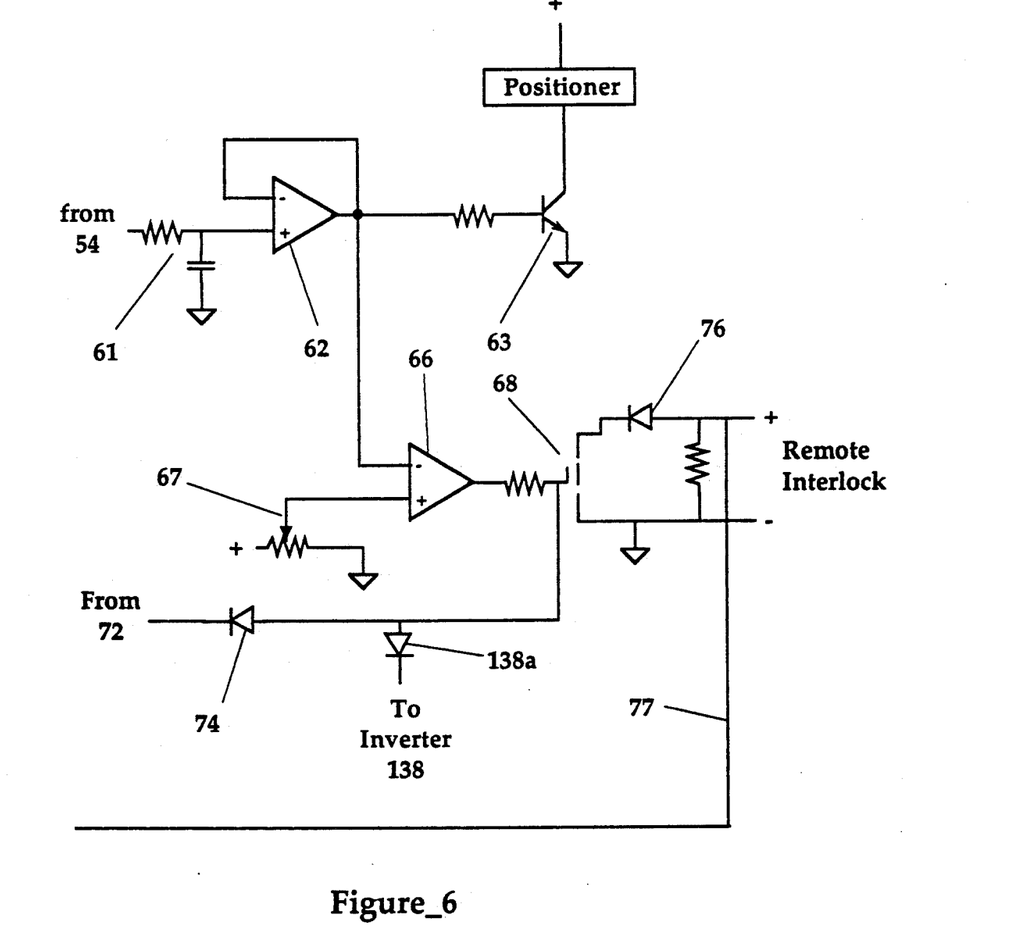

With regard to FIGS. 5 and 6, the photodetector 46 of the electronic circuit includes a pair of light sensitive diodes 50 and 52, each being tuned by filtering or the like to be sensitive in the electromagnetic spectrum generally corresponding to black body radiation in the operating temperature range of laser surgical instruments. The light sensitive diodes are arranged so that diode 50 receives the axial portion of the emission beam from the delivery system, while the diode 52 receives the peripheral portion of the emission beam. The signal from each diode is fed to a respective buffering amplifier 51 and 60, and thence to the positive and negative inputs of operational amplifier 53. The amplifier 53 subtracts the peripheral diode signal from the axial diode signal to adjust for differing delivery system optical fiber diameters, producing a temperature sensor signal that is accurate for a wide variety of optical fiber delivery systems. An variable voltage reference 55 provides an adjustable gain control for the amplifier 53 to permit selection of the magnitude of the system response to the temperature sensor signal, as will be explained in the following description. The output of the operational amplifier 53 is conducted to one side of switch 54.

The position sensor 56 of the shutter 39 includes an LED 57 closely spaced apart from a phototransistor 58, the gap therebetween receiving the rotating shutter wheel or arm. When the opaque portion of the shutter passes into the light path between the LED 57 and phototransistor 58, a voltage spike is input into dual monostable multivibrator 59. The dual monostable multivibrator 59 is actuated to produce to single pulse outputs, $Q_1$ and $Q_2$, in response to the voltage spike input. The pulse $Q_2$ is conducted to the actuating lead of solid state switch 54, so that the switch 54 is actuated whenever the shutter blocks the position sensor, and the signal from the temperature sensor is conducted through the switch 54.

With regard to FIG. 6, the temperature signal from switch 54 is fed through an RC integrating network 61 to an operational amplifier 62, the output of which is coupled to the base of drive transistor 63. Connected to the emitter-collector circuit of the transistor 63 is the positioner device 38 of the beam deflector 37 described previously. It may be appreciated that the component values are chosen so that the temperature control signal from switch 54 varies the conductivity of transistor 63 in proportion to the magnitude of the infrared temperature signal adjusted by the gain control 55. Thus, if the temperature of the delivery system is too high, the transistor 63 will be switched conductive to actuate the positioner 38 and extend the beam attenuator 37 farther into the beam path, reducing the laser power transmitted to the delivery system and decreasing the temperature. If the temperature signal is too low to switch on the transistor 63, the beam attenuator 37 is urged out of the laser beam path by built-in resilient means to allow the laser energy to be passed through the device unattenuated.

The circuit of the present invention may also be provided with safety features that interface with the existing laser to reduce the risk of accident or malfunction. The signal from operational amplifier 62 is fed to one input of operational amplifier 66, the other input being an adjustable voltage reference 67. The amplifier 66 compares the temperature control signal to the reference 67, and produces a signal if the temperature signal exceeds the preset level indicative of an unacceptably high temperature in the delivery system. The signal from amplifier 66 is conducted to the actuating input of a normally closed solid state switch 68. The switch 68 is connected across the standard remote interlock plug connection provided in virtually all laser systems, as for example by cable 85 connected between the device 21 and the remote interlock connector 86 of the laser (FIG. 2). Thus a signal from amplifier 66 will open the remote interlock and stop the laser immediately, before the overtemperature condition can cause damage.

The invention may also be provided with a further safety system, including a solid state temperature sensor 71 connected in series between a positive voltage and a resistor connected to ground (FIG. 5). The temperature sensor 71 is placed in contact with the heat sink 40 to monitor the temperature thereof. The signal from the temperature sensor 71 is connected to one input of operational amplifier 72, the other input being an adjustable reference voltage 73. The output signal of operational amplifier 72, which represents a comparison of the temperature sensor signal with a fixed reference, is conducted through blocking diode 74 to the actuating input of solid state switch 68. As a result, whenever the temperature of the heat sink exceeds a preset maximum level, the switch 68 is actuated to interrupt the remote interlock system and stop the laser immediately. Thus the invention is protected from failure due to overheating. Almost all lasers available commercially include some form of warning system to alert the user when the remote interlock system is interrupted.

As a further safety feature, the remote interlock may be provided with a diode 76 interposed in one side of the remote interlock circuit, the other side being connected to ground. The diode 76 produces a characteristic voltage drop, e.g. 0.6 v, when the switch 68 is connected across the remote interlock circuit of the laser and current is flowing therethrough. The diode leg is connected through line 77 to one input of operational amplifier 78, the other input being connected to a fixed voltage reference 79 that is slightly less than the diode voltage drop. Thus, whenever the switch 68 is connected to the laser remote interlock system, the diode voltage drop input is greater than the fixed reference input, and the amplifier produces no output signal. When the remote interlock circuit is disconnected from the invention, the fixed voltage input 79 causes the amplifier to conduct, sending a signal to alarm 81. The alarm 81 may comprise audio and/or visual alarm means to alert the laser user that the proper connection to the remote interlock has not been made, and that the remote interlock safety system cannot function.

Figure 7:
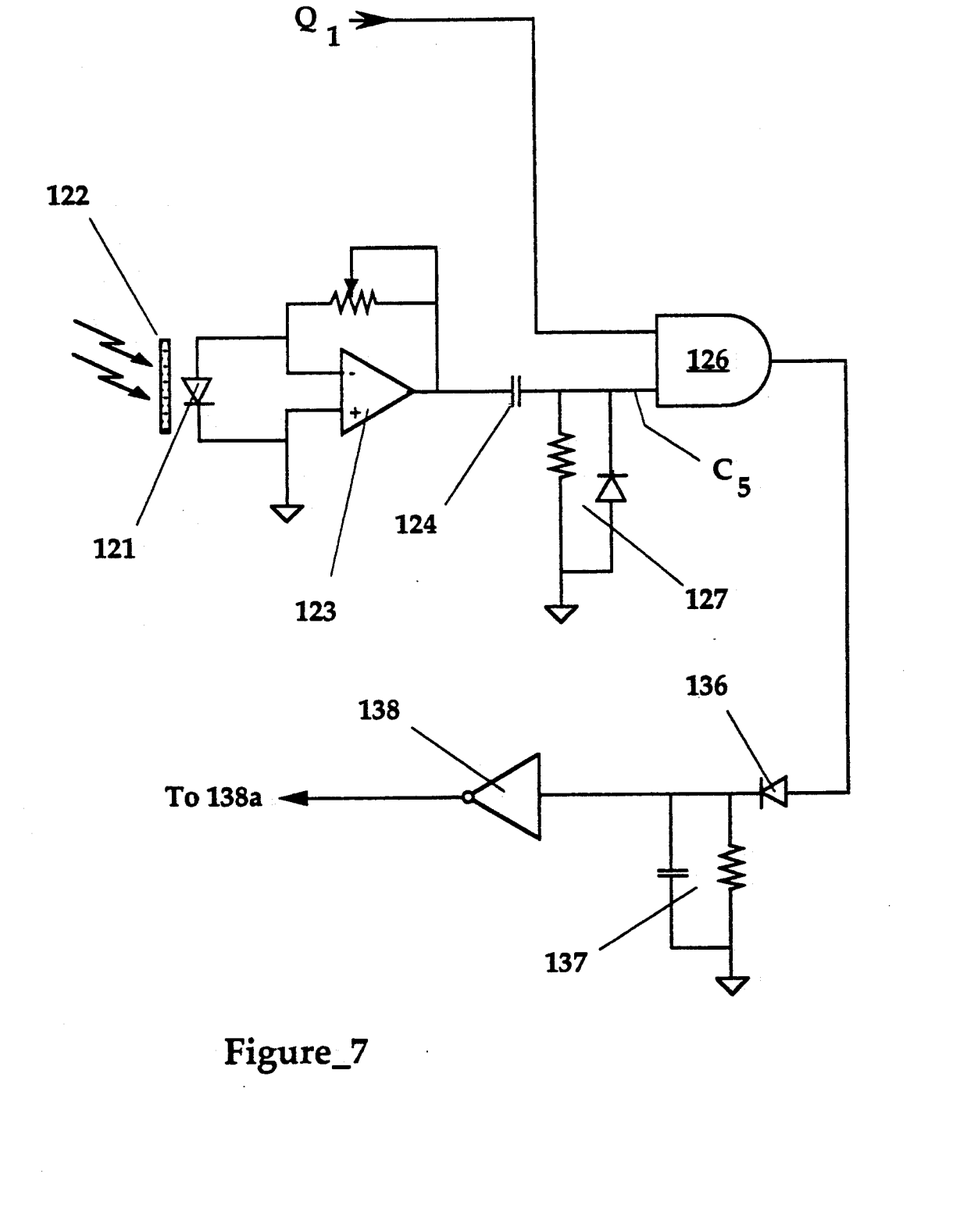
FIG. 7 is a schematic diagram of a electronic circuit for a further safety system of the present invention.

The present invention may also incorporate a further laser safety system that may obviate the need for laser safety eyewear in many laser procedures. This system, the laser radiation area detector, includes a photosensor 121 secured to the device 21 and directed obliquely toward a wall or ceiling surface in the room in which the laser is being used. The photosensor 121 may comprise a silicon photodiode or the equivalent, and is provided with a primary filter 122 that has a narrow optical passband in the range of the laser radiation. For example, commonly available filters transmit approximately 40% of light energy in the Nd:YAG output band, and only 1% of the remainder of the optical spectrum. Filters for other laser output bands are readily available.

The output of the photosensor, a current signal having a magnitude which is a function of the amount of laser light received by the sensor 121, is connected across the inputs of op amp 123. The output of op amp 123 is fed to differentiating capacitor 124, which in turn is connected to an input of AND gate 126.

Also connected to the same input is a parallel network comprised of a resistor and a diode extending to ground. The capacitor, in combination with this network, determines that a signal $C_5$ will appear on the input of gate 126 only when an abrupt negative change occurs in the amplitude of light in the narrow band of the laser output. The component values are chosen so that the output signal $C_5$ will comprise a brief pulse, on the order of microseconds, in response to the photosensor 121 receiving a sudden negative change in the ambient light level in the laser output band. Since virtually any broadband light source will emit some light energy in the laser output band, and this output can vary, it is important to distinguish sudden negative changes in the output band level that are indicative of laser pulse energy escaping into the area surrounding the laser itself.

Signal $Q_1$ from dual monostable multivibrator 59 is also input to the AND gate 126. When signals $Q_1$ and $C_5$ are coincident in time, AND gate 126 is actuated to produce an output signal during this signal convergence. Thus the gate 126 produces an output only when the photosensor 121 picks up an abruptly falling amplitude of area illumination in the laser output band, and only when this negative change occurs immediately after the cessation of a laser pulse, as the laser output is rapidly decreasing. Such convergence is a reliable indication of the escape of laser radiation into the area near the laser, and serves to discriminate laser radiation from background illumination.

The output of gate 126 is fed through diode 136 to an integrating network 137 comprised of a resistor and diode connected in parallel to ground. It is also connected to an inverting gate 138 which has its output connected through diode 138a to the actuating lead of solid state switch 68 (FIG. 6). The integrating network 137 determines that more than one output pulse from AND gate 126 is required to trigger a signal from inverter 138 to actuate switch 68, open the remote interlock circuit, and shut off the laser system. In the preferred embodiment the component values are chosen so that two output pulse from gate 126 are required to shut off the laser system.

Due to the fact that the safety circuit of FIG. 8 reliably distinguishes laser radiation from background light and ambient light, including fluorescent lights, surgical lights, photographic flash lamps, sunlight, and the like, the use of laser safety goggles may be obviated. For example, in laser surgery in which an endoscope or the like is used to perform procedures within a body cavity or enclosed space, the laser light will be contained within the patient if the delivery system is intact and the operating end is properly positioned within the enclosed operating area. If a fault should occur laser operation, such as a break in the optical fiber, or removal of the distal operating end from the patient, the laser radiation will be sensed immediately by the circuit of FIG. 7 and the laser will be shut off. The laser shutdown occurs so swiftly that operating room personnel can work safely without laser safety eyewear.

It may be appreciated that other safety systems such as the one depicted in FIG. 7 may be incorporated in the device 21 to enhance the safety and ease of operation of the laser 22. Alternatively, any or all of the systems described herein may be retrofit into an existing laser, or incorporated as original equipment during the manufacture of a laser.

The invention may include a control and display panel to permit selection of the maximum temperature levels of the surgical tool and the heat sink at which the system responds, as well as indicator lights or the like to inform the user of the operational status of the system. Such displays and controls are known in the prior art, and are available to any individual having ordinary skill in the art.

We claim:

1. An apparatus for controlling the output of a laser transmitted to a closed delivery system, including means for detecting the presence of radiation from the laser in the ambient light near the laser and generating an alarm signal, and means for stopping the output of the laser in response to said alarm signal.

2. A method for controlling the output of a laser coupled to a closed laser delivery system, comprising the steps of monitoring the ambient light in the area of the laser to detect laser wavelength radiation in the ambient light, and shutting off the laser radiation is detected in the ambient light.

3. A retrofit apparatus for use with an existing laser to modulate the laser output in response to the temperature of a laser powered tool, the laser including a remote interlock safety system containing a normally closed circuit that stops laser operation upon change to an open circuit condition, said apparatus including an apparatus housing external to the laser, a first optical coupler secured to said housing and adapted to be connected to the output of the existing laser, a second optical coupler secured to said housing and adapted to be connected to the laser powered tool, a beam path extending within said housing between said first and second couplers, means within said housing for selectively and variably attenuating the laser beam transmitted along said beam path, infrared sensor means directed toward said second optical coupler to receive infrared emissions from said laser powered tool and to generate a first temperature signal in response to said infrared emissions, means for periodically and briefly blocking said beam path to eliminate interference by the laser beam with said infrared sensor means, control means for receiving said first temperature signal and operating said means for selectively and variably attenuating the laser beam in proportion to said first temperature signal, and safety switch means adapted to be connected to the remote interlock safety system to open said normally closed circuit upon detecting an unsafe laser operating condition.

4. The apparatus of claim 3, further including means for electronically comparing said first temperature signal with a first adjustable reference signal and generating a drive signal conducted to said actuator means.

5. The apparatus of claim 3, further including a selectively reflective mirrir interposed in said beam path to direct said laser beam toward said second optical coupler, said selectively reflective mirror reflecting the laser wavelength and passing said infrared emissions, said infrared sensor being disposed to receive said infrared emissions through said selectively reflective mirror.

6. The apparatus of claim 3, wherein said beam deflector comprises a reflective member.

7. The apparatus of claim 6, further including an absorptive heat sink, said reflective member being disposed to reflect a variable portion of the laser beam toward said heat sink.

8. The apparatus of claim 7, further including second temperature sensing means operatively associated with said heat sink for producing a second temperature signal, and electronic means for comparing said second temperature signal with a second adjustable reference level and generating an alarm actuating signal.

9. The apparatus of claim 8, wherein the laser includes a remote interlock safety circuit, and further including switch means connected to the remote interlock safety circuit of the laser, said alarm actuating signal connected to the actuating lead of said switch means to open said switch means and said remote safety circuit and stop operation of the laser.

10. The apparatus of claim 9, further including maximum level detector means connected to receive said first temperature signal and to actuate said switch means when said first temperature signal exceeds a maximum level.

11. An apparatus used in combination with an existing laser having a remote interlock safety circuit, said apparatus for controlling the temperature of a laser tool, comprising a first optical coupler adapted to be connected to the output of the laser, a second optical coupler adapted to be connected to the laser tool, a beam path extending between said first and second couplers, first temperature sensing means for sensing the temperature of the laser tool and generating a first temperature signal, means for selectively and variably attenuating the laser beam transmitted along said beam path in response to said temperature signal, switch means connected to the remote interlock safety circuit of the laser to open said remote safety circuit and stop operation of the laser, and means for detecting the presence of radiation from the laser in the ambient light near the laser and generating an alarm signal, said alarm signal connected to said switch means to cause immediate laser shutoff.

12. The apparatus of claim 4, wherein said means for detecting the presence of radiation from the laser in the ambient light includes a photosensor tuned to the laser output band and directed to receive ambient light, said photosensor generating a sensor signal, and electronic means for receiving said sensor signal and discriminating laser radiation from background light.

13. The apparatus of claim 12, wherein said electronic means for discriminating laser light includes means for briefly and periodically interrupting the laser beam and for generating a timing pulse corresponding to each interruption.

14. The apparatus of claim 13, wherein said electronic means further includes means for detecting an abrupt decrease in said sensor signal coincident with a timing pulse, and for generating said alarm signal upon detecting coincidence of said timing pulse and said abrupt decrease in said sensor signal.

15. A method for controlling the output of a laser coupled to a laser delivery system, comprising the steps of monitoring the temperature of the delivery system and generating a temperature signal in response thereto, and moving a laser beam deflector in and out of the laser beam path in proportion to said temperature signal to deflect a portion of the laser beam and control the temperature of the delivery system, further including the step of periodically interrupting the laser beam to eliminate laser interference during the step of monitoring the temperature of the delivery system, and directing a laser wavelength-sensitive photosensor toward the ambient light in the area of the laser, and shutting off the laser when laser radiation is present in the ambient light.

16. The method of claim 15, further including the step of generating a photosensor signal and connecting the photosensor signal to the remote interlock safety system of the laser to shut off the laser.

17. The method of claim 16, further including the step of the photosensor signal to detect an abrupt decrease in the amplitude of the signal coincident with periodic interruption of the laser beam.

* * * * *